US007780352B2

(12) United States Patent
Fox et al.

(10) Patent No.: US 7,780,352 B2
(45) Date of Patent: Aug. 24, 2010

(54) RADIATION SYSTEM AND RADIATION BEAM QUALITY DETECTOR AND METHOD

(75) Inventors: Timothy R. Fox, Chicago, IL (US); David T. Nisius, Des Plaines, IL (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 12/048,005

(22) Filed: Mar. 13, 2008

(65) Prior Publication Data

US 2008/0226038 A1 Sep. 18, 2008

Related U.S. Application Data

(60) Provisional application No. 60/894,807, filed on Mar. 14, 2007.

(51) Int. Cl.
*G01D 18/00* (2006.01)
(52) U.S. Cl. ............................ 378/207; 378/156
(58) Field of Classification Search ......... 378/156–159, 378/207
See application file for complete search history.

(56) References Cited

U.S. PATENT DOCUMENTS 6,454,460 B1 * 9/2002 Ramanathan et al. ....... 378/207

6,633,627 B2  10/2003 Horiuchi

OTHER PUBLICATIONS

Related International Patent Application No. PCT/US08/56967; Search Report dated Aug. 14, 2008, 2 pgs.

* cited by examiner

*Primary Examiner*—Jurie Yun
(74) *Attorney, Agent, or Firm*—Fitch, Even, Tabin & Flannery

(57) ABSTRACT

A detector array is disposed relative to a radiation source such that radiation from the radiation source over a predetermined time period is substantially similar across the detector array. The detector array includes radiation detectors operatively coupled to detector electronics. The radiation filter material is disposed at least partially between the radiation source and the detector array such that different portions of the detector array are exposed to radiation from the radiation source through either different radiation filter material thicknesses or different radiation filter material compositions during the predetermined time period. So configured, information regarding the radiation such as beam quality information for radiation pulses is collected and used to confirm the quality of the radiation source or to adjust data collected by the radiation system.

16 Claims, 7 Drawing Sheets

US 7,780,352 B2

RADIATION SYSTEM AND RADIATION BEAM QUALITY DETECTOR AND METHOD

RELATED APPLICATION(S)

This application claims the benefit of U.S. Provisional application No. 60/894807, filed Mar. 14, 2007, which is incorporated by reference in its entirety herein.

TECHNICAL FIELD

This invention relates generally to radiation systems and more particularly to sensing radiation beam quality in radiation systems.

BACKGROUND

Electronic x-ray imaging systems, including digital radiography ("DR") and computed tomography ("CT") systems, usually employ a reference detector system to monitor the x-ray source. In a direct current ("DC") x-ray source (conventional x-ray tube) that runs continuously, the reference detector is used to monitor the total output of the source during each sample (a CT view or a DR line) acquired by the x-ray detector during a multi-sample scan. Except for electrical glitches (such as arcs) in the x-ray tube, the variations of x-ray energy output are expected to be relatively slow, and a straightforward x-ray detector mounted close to the source (avoiding interference from whatever object is in the x-ray beam) generally suffices to measure the total energy output of the radiation source. Such a reference detector, however, cannot provide beam-quality information regarding the radiation beam produced by the radiation sources.

As opposed to typical DC x-ray sources, high-energy x-ray sources are typically electron linear accelerators that deliver short-duration pulses of approximately mono energetic electrons to an appropriate target, such as tungsten. Inside the x-ray source, a narrow high-voltage pulse is applied to a high-frequency generator that is coupled to a resonant microwave cavity to accelerate the electrons via very high electric fields. Due to practical limitations of the pulse generator, microwave generator, and cavity, there is some level of uncontrolled variation in both the total energy contained in each pulse of electrons and the effective acceleration voltage (which determines the electrons' kinetic energy) in each pulse. This uncontrolled variation typically increases if the pulse train is not at a constant frequency.

There is a current trend towards material characterization (distinguishing different ranges of atomic number as well as total amounts of material struck by the radiation beam) by comparing x-ray transmission signals at two different energy settings of the x-ray source for a megavolt DR scanner, a scan requiring relative motion between the x-ray system and the object: either the x-ray system moves past a stationary object, or the object moves past a stationary x-ray system. In general, this can be done in one of three ways. First, one source and detector can run two separate scans on the same object where in between the two scans, the energy setting is changed on the single source. Second, two sources, each with its own detector, collect separate images of the same object in one scan of the object. In one example, each of the two detectors may be optimized separately for one of the two sources. Normally, the two imaging systems are separated by a reasonable distance in the direction of travel. Third, one source, capable of rapidly switching between two energy settings, produces an image in one detector where every other line corresponds to one of the two energy settings.

In all cases, the material discrimination is based on comparing the attenuations of the radiation as it passes through the object, as a function of position, for the two source energies. For an x-ray source based on Bremsstrahlung effects, each energy setting for the source determines the source's maximum energy in a broad energy spectrum. For a an x-ray source in the form of a DC tube, the source's maximum energy is determined by the DC voltage applied from a cathode to anode in the tube. For a pulsed accelerator x-ray source, the maximum energy is determined by the relatively narrow range of energy in the accelerated electron beam that hits the target. In many applications, the accuracy or sensitivity of the discrimination depends on the repeatability of these maximum energies or other details of the two spectra.

BRIEF DESCRIPTION OF THE DRAWINGS

The above needs are at least partially met through provision of the radiation system and radiation beam quality detector and method described in the following detailed description, particularly when studied in conjunction with the drawings, wherein.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION OF THE PREFERRED EMBODIMENTS

Generally speaking, pursuant to these various embodiments, a radiation system may include a detector array disposed relative to a radiation source such that radiation from the radiation source over a predetermined time period is substantially similar across the detector array. The detector array includes radiation detectors operatively coupled to detector electronics. The radiation filter material is disposed at least partially between the radiation source and the detector array such that different portions of the detector array are exposed to radiation from the radiation source through either different radiation filter material thicknesses or different radiation filter material compositions during the predetermined time period.

So configured, the radiation system may be able to detect beam quality for its radiation source. This information can be used to test the radiation source for quality over time or at the manufacturing stage of the radiation system. The radiation system may also be able to test beam quality between pulses of a radiation source to assure consistent quality of performance of the radiation source over time or to make adjustments to account for errors relating to inconsistent radiation source operation.

Figure 1:
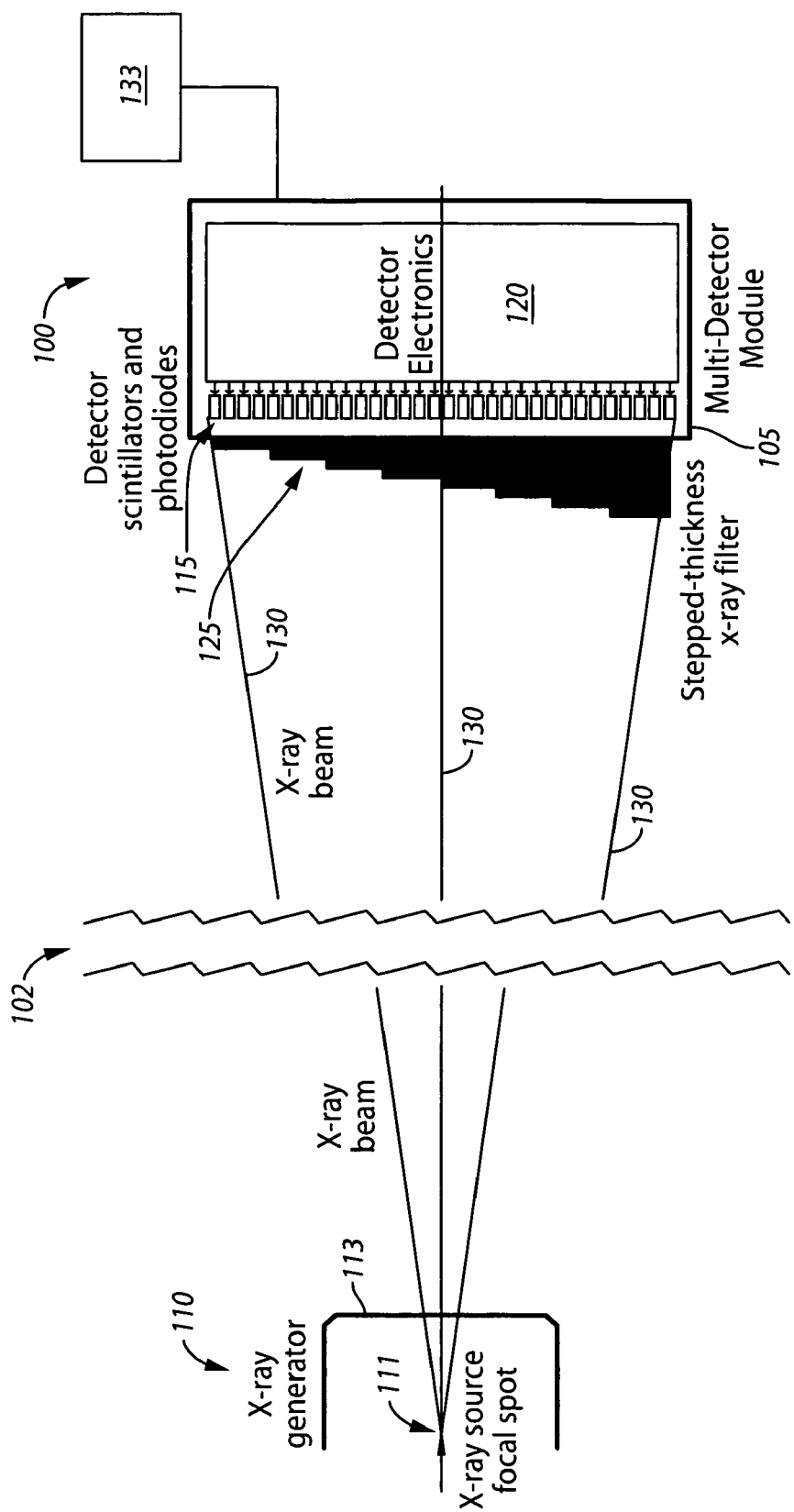
FIG. 1 comprises a block diagram of a radiation system as configured in accordance with various embodiments of the invention.

These and other benefits may become clearer upon making a thorough review and study of the following detailed description. Referring now to the drawings, and in particular to FIG. 1, an apparatus 100 for detecting beam quality in a radiation system 102 includes a detector array 105 disposed relative to a radiation source 110 such that radiation from the radiation source 110 over a predetermined time period is substantially similar across the detector array 105. The detector array 105 includes radiation detectors 115 operatively coupled to detector electronics 120. The radiation filter material 125 is disposed at least partially between the radiation source 110 and the detector array 105 such that different portions of the detector array 125 are exposed to radiation from the radiation source 110 through either different radiation filter material thicknesses or different radiation filter material compositions during the predetermined time period. The detector electronics 120 are in communication with a computing device 133 that calculates a value related to beam quality of the radiation 130 from the radiation source 110 based at least in part on different signals from different portions of the detector array 105.

Figure 2:
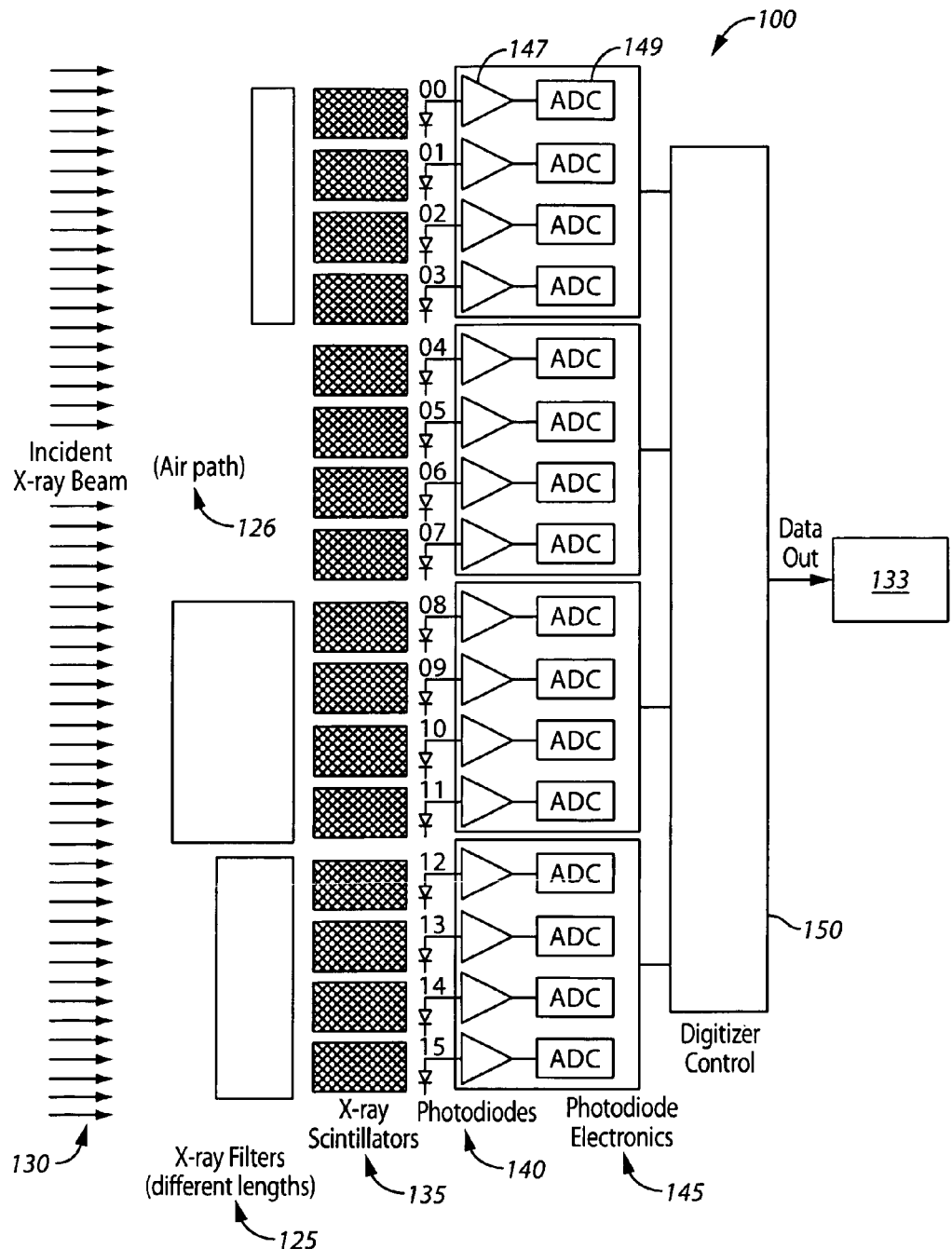
FIG. 2 comprises a block diagram of a detector system as configured in accordance with various embodiments of the invention.

With reference to FIG. 2, the detector array 105 includes a plurality of x-ray scintillators 135 disposed opposite of a radiation filter material 125 relative to the radiation 130. Photodiodes 140 are optically coupled to the scintillators 135 to collect light emanating therefrom. The photodiodes are connected to photodiode electronics 145. The photodiode electronics include an amplifier 147 and analog to digital converters 149. Photodiode electronics are in communication with digitizer control 150. Digitizer control 150 is in communication with the computing device 133.

So configured, radiation 130 hitting the scintillators 135 causes the scintillators to create light that strikes the photodiodes 140. The photodiodes 140 convert the light output from the scintillators 135 into an electrical signal such as a current or voltage. The signal from the photodiodes 140 is amplified by the amplifier 147 and converted from an analog format into digital signals by the analog to digital converter 149. The amplifier 147 is typically an integrating amplifier that collects the current or voltage from the photodiodes 140 and produces an output corresponding to the total current or voltage collected from the photodiodes 140 over a given time period. The output from the amplifier 147 in this example then corresponds to the total radiation energy received by the scintillators 135 in a given area of the radiation detector array 105. The detector electronics 120 are in communication with the computing device 133 that calculates a value related to beam quality of the radiation 130 from the radiation source 110 based at least in part on different signals from different portions of the detector array 105.

Those skilled in the art will recognize and understand that such an apparatus 100 may be comprised of a plurality of physically distinct elements as is suggested by the illustration shown in FIG. 2. It is also possible, however, to view this illustration as comprising a logical view, in which case one or more of these elements can be enabled and realized via a shared platform. It will also be understood that such a shared platform may comprise a wholly or at least partially programmable platform as are known in the art.

The value related to beam quality of radiation from the radiation source 110 may be a half value parameter for the radiation from the radiation source 110. The term beam quality refers generally to the ability of a radiation beam to penetrate into a material or the ability of different materials to absorb energy from the radiation beam. Accordingly, the term half value refers to the depth to which a radiation beam may penetrate a material until the radiation beam loses one half of its total energy. The quality of a given radiation beam will affect the beam's ability to create images and the ability of the radiation system to make determinations relating based on information collected from the radiation system.

Figure 3:
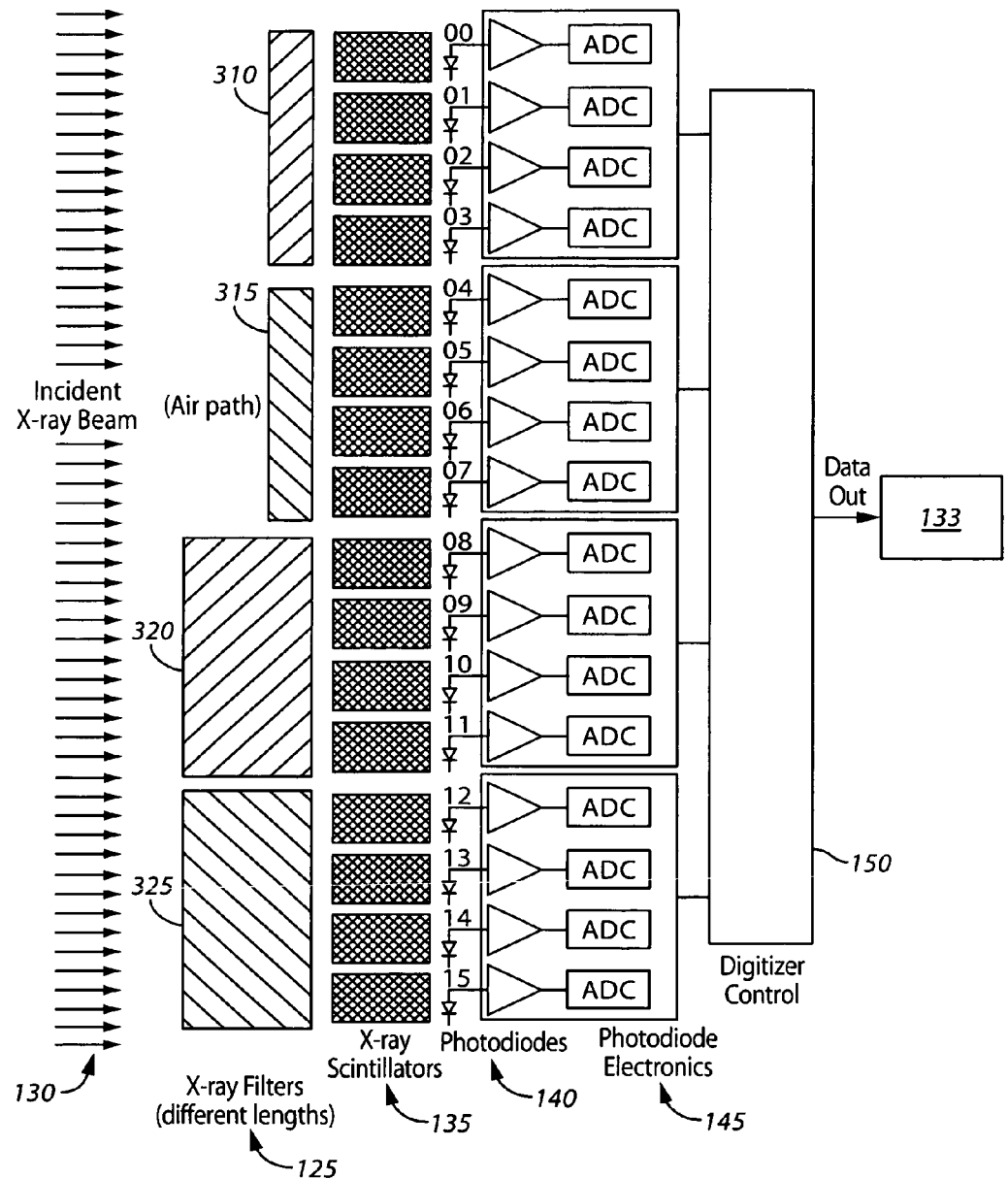
FIG. 3 comprises a block diagram of a detector system as configured in accordance with various embodiments of the invention.

The beam quality of the radiation beam can be determined by comparing the strength of the radiation beam after it has passed through a variety of materials. For example, the radiation filter material 125 disposed in front of the detector electronics 105 may include a variety of materials or material thicknesses. By one approach, the radiation filter material 125 shown in FIG. 2 is disposed such that at least a portion of the detector array is unblocked from the radiation source 110. By another approach, the radiation filter material 125 may include a plurality of thicknesses of the material disposed between the radiation source 110 and a detector array 105 as illustrated in the example of FIG. 1. Such an arrangement may be called a stepped wedge of material. The radiation filter material 125 may comprise a variety of compositions including at least one of the group comprising steel, aluminum, copper, a copper alloy, brass, bronze, a heavy metal, tungsten, lead, an organic material, and plastic. For example, as illustrated in FIG. 3, two different filter material thicknesses and two different filter material compositions are used. Filter material portions 310 and 315 are of common thickness; however, filter material portions 310 and 315 are of different materials. Similarly, filter material portions 320 and 325 are of approximately the same thickness. Filter material portions 310 and 320 are of the same material and filter material portions 315 and 325 are of the same material that differs from the material of filter material portions 310 and 320. The combination of material type and material thickness may be adjusted to fit a given application.

Different portions of the detector array 105, for example different sets of scintillators 135, will then be exposed to different radiation energies depending on the filter material type or filter material thickness through which the radiation beam must pass before intercepting the scintillators 135. These sensed radiation energies may be compared to tables of expected energies based on the energy level of the radiation beam and the filter material types and thicknesses to determine a value related to beam quality, such as the half value layer parameter.

Figure 4:
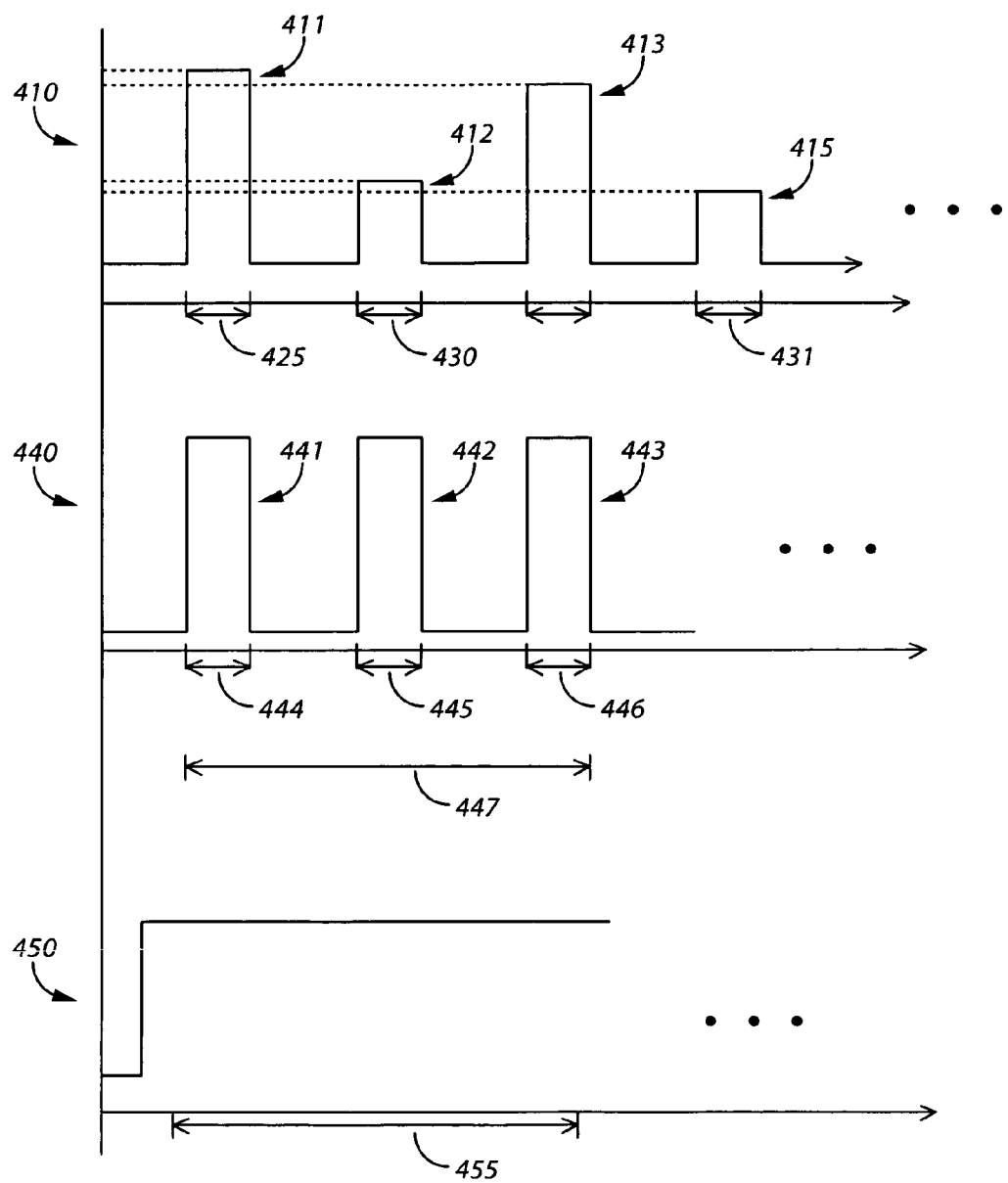
FIG. 4 comprises representations of radiation source pulse trains as may be used in radiation systems.

The detector electronics 120 may be configured to collect and analyze radiation information over a variety of time periods to fit the needs of any particular system. For example, the predetermined time period over which information is collected may include any of a number of time periods including over a single pulse from the radiation source, over at least two high energy pulses from the radiation source, over at least two low energy pulses from the radiation source, and over a time during a nominally constant radiation pulse. FIG. 4 illustrates some example radiation output patterns. The graph designated 410 illustrates a pulse train with high energy pulses 411, 413, and 415 alternating with low energy pulses 412 and 414. These pulses are typically about four microseconds wide, separated by three milliseconds. The higher energy pulses are typically in the range of about nine mega electron volts (or, by another approach, six mega electron volts), and low energy pulse are typically about six mega electron volts (or, three mega electron volts, respectively). To determine the quality of the radiation pulses or to determine whether the quality is being consistent between radiation pulses for such a pulse train, the system electronics are configured to determine and collect information from the system during the time periods in which the high energy pulses are being provided, for example, at time period 425. The system may also collect information regarding the radiation beam during the low energy pulses, for example, during time period designated 430. So configured, the system is able to determine the energy variations among the pulses. By another approach, the system may be configured to collect information regarding the radiation beam over more than one high or low energy pulse, for example, by integrating energy information during time periods 430 and 431 to determine an average or total energy output over those pulses 412 and 414.

The graph designated with reference numeral 440 illustrates a pulse train with generally consistent radiation pulses 441, 442, and 443. For such a pulse train, the system may be configured to determine and collect information during the time period 444, 445, and 446 of each pulse 441, 442, and 443. By a different approach, the system may be configured to determine and collect information during a longer time period 447 to determine an average energy output for the system. The graph designated with reference numeral 450 illustrates a nominally constant radiation pulse. In such a configuration, the system may collect information over a time period 455 that may be designated by a user to fit a given system.

Figure 5:
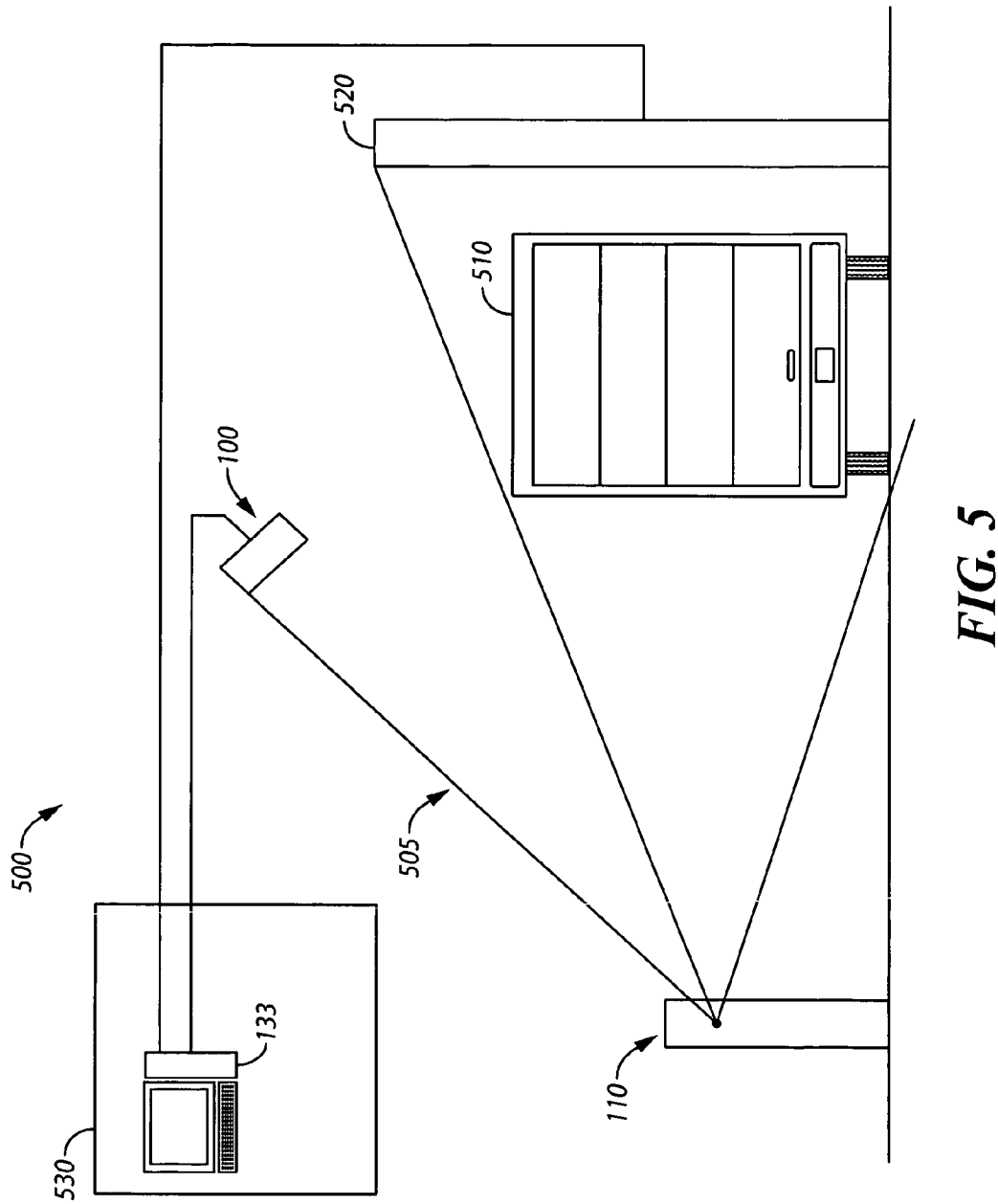
FIG. 5 comprises a block diagram of a detector system as configured in accordance with various embodiments of the invention.

One example system 500 built according to the teachings of this disclosure will be described with reference to FIG. 5. The radiation source 110 emits radiation 505 toward a truck 510 such that radiation penetrating the truck 510 is sensed by a detector 520. Such a system may be employed to detect illegal or dangerous materials in shipping containers such as those carried by trucks or by ship. The radiation detector 100 is disposed to intercept the radiation 505 such that the radiation 505 energy intercepted by the detector 100 is approximately the same and to not disrupt radiation 505 from hitting the target, in this example, the truck 510. The detector 520 collects information regarding the radiation 505 passing through the truck 510 and passes that information to a computing device 133 in a control room 530. The information may be used to create an image of the truck 510 to analyze the makeup of materials on the truck 510. For example, the system 500 may be configured to subject the truck 510 to two different radiation energies to detect and identify material that may be used in a nuclear device. The computing device 133 will compare the differences in the absorption of the two energies of radiation passing through the truck 510 to known values for various materials to determine the presence of such materials on the truck 510.

Because the determination of types of materials is dependent on the energy values of the radiation 505, the beam quality checking apparatus 100 is in communication with the computing device 133 to provide accurate measurement of the beam quality and energy levels of the two radiation energies used to scan the truck 510. The beam quality information may be used by the computing device 133 to provide increased accuracy of the determination of materials in the truck 510.

Those skilled in the art will recognize and appreciate that the computing device can comprise a fixed-purpose hard-wired platform or can comprise a partially or wholly programmable platform completely separate from the apparatus 100 or radiation detector 520, or the computing device 133 may be integrated into such structures. All of these architectural options are well known and understood in the art and require no further description here.

Figure 6:
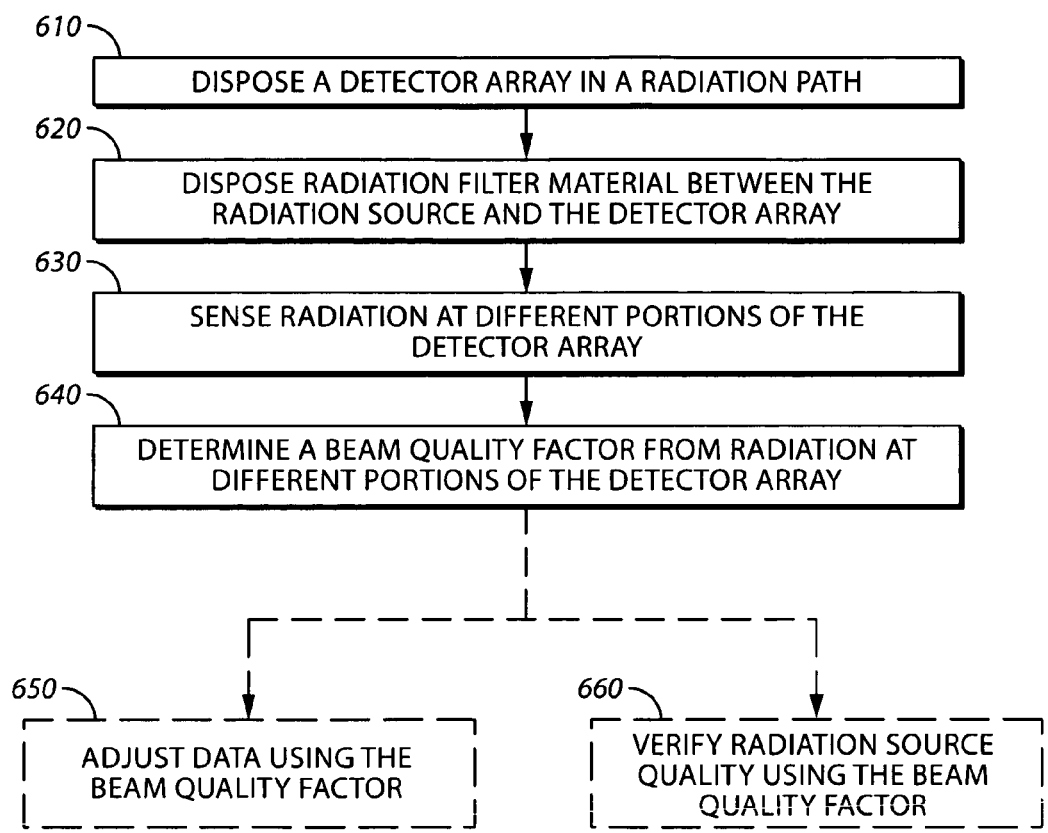
FIG. 6 comprises a flow diagram as configured in accordance with various embodiments of the invention.

A method of measuring variation in radiation output in a radiation device will be described with reference to FIG. 6. A detector array 105 is disposed 610 in a path of radiation 130 from a radiation source 110. At least one radiation filter material is disposed 620 between the radiation source and at least a portion of the detector array 105. The radiation filter material 125 may be disposed in a number of ways to provide various filtering of the radiation including disposing a first radiation filter material between a first portion of the detector array and the radiation source leaving at least a second portion of the detector array exposed to the radiation source without the radiation filter material such that a more direct reading or sensing of the radiation 130 may be taken. By another approach, a first radiation filter having a first thickness may be disposed between a first portion of the detector array and the radiation source, and a second radiation filter having a second thickness may be disposed between a second portion of the detector array and the radiation source. By yet another approach, a first radiation filter having a first composition may be disposed between a first portion of the detector array and the radiation source, and a second radiation filter having a second composition may be disposed between a second portion of the detector array and the radiation source. Any combination of the above approaches may be employed in the same system.

As such, radiation 130 is sensed 630 at different portions of the detector array 105 corresponding to which radiation filter material 125 is disposed between the radiation source 110 and the detector array 105 portion during a predetermined time period. For instance, an integrating amplifier may capture an output from a detector array portion over the predetermined time period. As described above, the predetermined time period may be configured to suit the particular system, including, for example, at least one of a group comprising a single pulse of the radiation source, at least two high-energy pulses from the radiation source, at least two low-energy pulses from the radiation source, and a time over a nominally constant radiation output.

The system compares radiation sensed at the portions of the detector array 105 to determine 640 a beam quality factor for the radiation over the predetermined time period. For example, a half-value layer measurement may be determined for the radiation filter material and the second radiation filter material for the predetermined time period. The method may then continue on to adjust 650 data produced by the radiation device using the beam quality factor for the radiation over the predetermined time period. For example, the beam quality information for both high and low energy radiation pulses may be used to provide more accurate material determinations. By another approach, the method may verify 660 a quality of a radiation source for the radiation device using the beam quality factor for the radiation over the predetermined time period. So configured, the radiation device may be configured during manufacture, or the radiation source may be replaced if its performance is inadequate.

Figure 7:
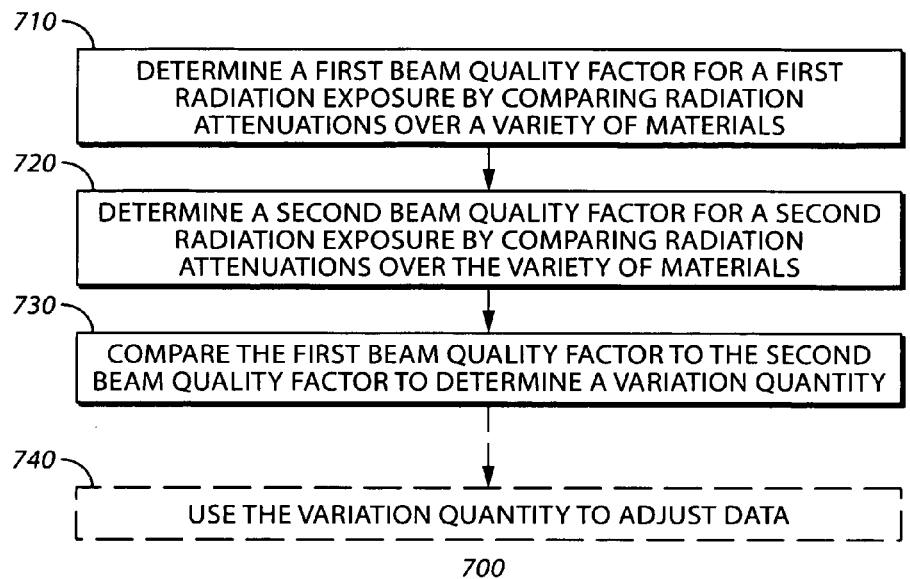
FIG. 7 comprises a flow diagram as configured in accordance with various embodiments of the invention.

FIG. 7 illustrates a method 700 of verifying quality of a radiation system. A first beam quality factor is determined 710 for a first radiation exposure by comparing radiation attenuations over a variety of materials. A second beam quality factor is determined 720 for a second radiation exposure by comparing radiation attenuations over the variety of materials. The first beam quality factor is compared 730 to the second beam quality factor to determine a variation quantity between the first radiation exposure and the second radiation exposure. The radiation attenuations may be compared over at least two components of a multi-component filter. The filter may include at least one of an air gap, at least two thicknesses of filter material, and at least two filter materials. The variation quantity may be used 740 to adjust data captured at least one of the first radiation exposure and the second radiation exposure. For example the variation quantity may be used to adjust the readings used to determine a substance or material scanned by the radiation system.

Figure 8:
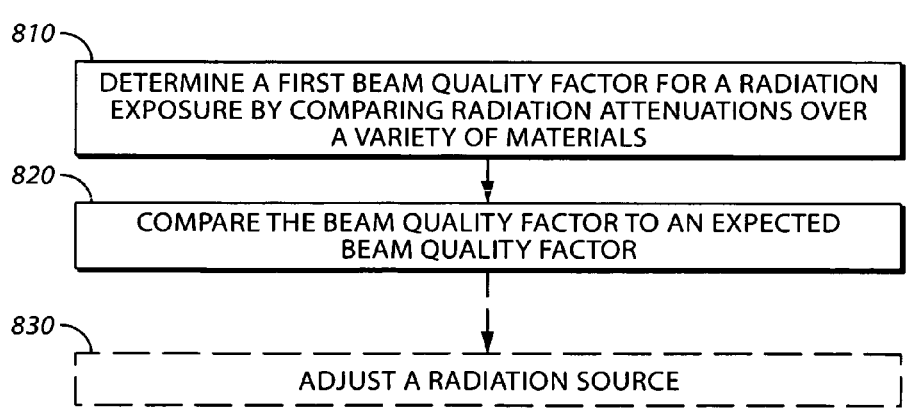
FIG. 8 comprises a flow diagram as configured in accordance with various embodiments of the invention.

FIG. 8 illustrates another method 800 of verifying the quality of a radiation system. This method 800 comprises determining 810 a first beam quality factor for a first radiation exposure by comparing radiation attenuations over a variety of materials. Then, the first beam quality factor is compared 820 to an expected beam quality factor for the radiation system. The first beam quality factor is determined according to the teachings of this disclosure. The method 800 may then include adjusting 830 a radiation source of the radiation system based at least in part on a difference between the first beam quality factor and the expected beam quality factor.

So configured, a radiation system according to these teachings may be able to detect beam quality for its radiation source. This information can be used to test the radiation source quality over time or at the manufacturing stage of the radiation system. The radiation system may also be able to test beam quality between pulses of a radiation source to assure consistent quality of performance of the radiation source over time or to make data adjustments to account for errors relating to inconsistent radiation source operation. For example, material identification analysis may be corrected using the beam quality information for such a system.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. An apparatus for detecting beam quality in a radiation system comprising:
   a first detector array disposed relative to a radiation source to intercept radiation energy from the radiation source that also intercepts a target object to thereby image the target object;
   a second detector array disposed relative to the radiation source to also intercept radiation energy from the radiation source while the first detector array images the target object such that radiation from the radiation source over a predetermined time period is substantially similar across the second detector array, the second detector array comprising radiation detectors operatively coupled to detector electronics;
   a radiation filter material disposed at least partially between the radiation source and the second detector array and such that the radiation filter material does not disrupt radiation from the radiation source from intercepting the target object while the first detector array images the target object, such that different portions of the second detector array are exposed to radiation from the radiation source through at least one of a group comprising different radiation filter material thicknesses and different radiation filter material compositions during the predetermined time period.

2. The apparatus of claim 1 wherein the detector electronics comprise integrating amplifiers collecting information from radiation detectors during the predetermined time period.

3. The apparatus of claim 1 wherein the radiation filter material is disposed such that at least a portion of the second detector array is unblocked from the radiation source.

4. The apparatus of claim 1 wherein the radiation filter material comprises a plurality of thicknesses disposed between the radiation source and the second detector array.

5. The apparatus of claim 1 wherein the radiation filter material compositions comprise at least one of a group comprising steel, aluminum, copper, a copper alloy, brass, bronze, a heavy metal, tungsten, lead, an organic material, and plastic.

6. The apparatus of claim 1 wherein the predetermined time period comprises a time period encompassing at least one of a group comprising a single pulse from the radiation source, at least two high-energy pulses from the radiation, at least two low-energy pulses from the radiation source, and a time over a nominally constant radiation output.

7. The apparatus of claim 1 wherein the detector electronics are operatively coupled to a computing device that calculates a value related to beam quality of the radiation from the radiation source based at least in part on different signals from different portions of the second detector array.

8. The apparatus of claim 7 wherein the value related to beam quality of radiation from the radiation source comprises a half-value layer parameter for the radiation from the radiation source.

9. The apparatus of claim 7 wherein the computing device is operatively coupled to the radiation system such that the radiation system uses the value related to beam quality of the radiation from the radiation source to adjust data produced by the radiation system.

10. The apparatus of claim 7 wherein the computing device is operatively coupled to the radiation system such that the radiation system uses the value related to beam quality of the radiation from the radiation source to verify a quality of the radiation source.

11. A method of measuring variation in radiation output in a radiation device comprising:
   disposing a first detector array in a path of radiation from a radiation source to intercept radiation energy from the radiation source that also intercepts a target object;
   disposing a second detector array in the path of radiation from the radiation source;
   disposing at least one radiation filter material between the radiation source and at least a portion of the second detector array such that the at least one radiation filter material does not disrupt radiation from the radiation source from intercepting the target object;
   while sensing at the first detector array the radiation energy that also intercepts the target object in order to image the target object, also sensing radiation at different portions of the second detector array corresponding to which radiation filter material is disposed between the radiation source and the second detector array portion during a predetermined time period;

comparing radiation sensed at the portions of the second detector array during the predetermined time period to determine a beam quality factor for the radiation over the predetermined time period.

12. The method of claim 11 wherein disposing at least one radiation filter material between the radiation source and at least a portion of the second detector array further comprises at least one of a group comprising:
   disposing a first radiation filter material between a first portion of the second detector array and the radiation source leaving at least a second portion of the second detector array exposed to the radiation source without the radiation filter material;
   disposing a first radiation filter having a first thickness between a first portion of the second detector array and the radiation source and disposing a second radiation filter having a second thickness between a second portion of the second detector array and the radiation source;
   disposing a first radiation filter having a first composition between a first portion of the second detector array and the radiation source and disposing a second radiation filter having a second composition between a second portion of the second detector array and the radiation source.

13. The method of claim 11 wherein the step of sensing radiation at different portions of the second detector array corresponding to which radiation filter material is disposed between the radiation source and the second detector array portion during a predetermined time period further comprises capturing at an integrating amplifier an output from a second detector array portion over the predetermined time period wherein the predetermined time period comprises at least one of a group comprising a single pulse of the radiation source, at least two high-energy pulses from the radiation source, at least two low-energy pulses from the radiation source, and a time over a nominally constant radiation output.

14. The method of claim 11 wherein the step of comparing radiation sensed at the portions of the second detector array during the predetermined time period to determine a beam quality factor for the predetermined time period comprises determining a half-value layer measurement for the radiation through a first radiation filter material and a second radiation filter material for the predetermined time period.

15. The method of claim 11 further comprising adjusting data produced by the radiation device using the beam quality factor for the radiation over the predetermined time period.

16. The method of claim 11 further comprising verifying a quality of a radiation source for the radiation device using the beam quality factor for the radiation over the predetermined time period.

* * * * *